United States Patent [19]

Butler

[11] 4,357,597

[45] Nov. 2, 1982

[54] PALM-POSITIONING AND SYSTEM-ACTUATING MECHANISM

[75] Inventor: Marlow D. Butler, Portland, Oreg.

[73] Assignee: Palmguard, Inc., Beaverton, Oreg.

[21] Appl. No.: 181,479

[22] Filed: Aug. 26, 1980

[51] Int. Cl.³ .............................................. G06K 9/32
[52] U.S. Cl. ............................................... 340/146.3 E
[58] Field of Search .......... 340/146.3 E, 3 MA, 825.3, 340/825.31, 825.32, 825.33, 825.34

[56] References Cited

U.S. PATENT DOCUMENTS

| | | | |
|---|---|---|---|
| 3,576,537 | 4/1971 | Ernst | 340/146.3 E |
| 3,576,538 | 4/1971 | Miller | 340/146.3 E |
| 3,581,282 | 5/1971 | Altman | 340/146.3 E |
| 3,614,737 | 10/1971 | Sadowsky | 340/146.3 E |
| 3,619,060 | 11/1971 | Johnson | 340/146.3 E |
| 3,639,905 | 2/1972 | Yaida et al. | 340/146.3 E |
| 3,648,240 | 3/1972 | Jacoby et al. | 340/146.3 E |
| 3,668,633 | 6/1972 | Sadowsky | 340/146.3 E |
| 3,804,524 | 4/1974 | Jocoy et al. | 340/146.3 E |
| 4,032,889 | 6/1977 | Nassimbene | 340/146.3 E |
| 4,186,378 | 1/1980 | Moulton | 340/146.3 E |

*Primary Examiner*—Leo H. Boudreau
*Attorney, Agent, or Firm*—Adrian J. LaRue

[57] ABSTRACT

A palm-positioning and system-actuating mechanism properly positions a person's palm in a palm-positioning area of an electronics module of an identification system and activates the means for storing in coded form the palm of a person or for comparing the person's palm with the stored coded palm for positive identification.

8 Claims, 3 Drawing Figures

PALM-POSITIONING AND SYSTEM-ACTUATING MECHANISM

BACKGROUND OF THE INVENTION

U.S. Pat. No. 4,186,378 discloses an identification system which scans an image of a person's palm and then stores in memory the palm in coded form for future positive identification of that person. In order to properly store the person's palm in coded form and to compare his palm with his coded palm for positive identification, his palm must be accurately positioned in the palm-positioning area of the electronics module of the identification system.

SUMMARY OF THE INVENTION

The present invention relates to a positioning and actuating mechanism and more particularly to a positioning and actuating mechanism for properly positioning a person's palm in the palm-positioning area of the electronics module of an identification system and for activating the means for storing in coded form the palm of the person or for comparing the person's palm with the stored coded palm for positive identification.

The present invention is best realized by a palm-positioning area on an electronics module which includes an opening in a panel over which a person's palm is positioned. A thumb and forefinger-engaging member is pivotally mounted on the panel adjacent the opening. A switch-actuating means is mounted on the pivot. Sufficient play is provided at the pivot to enable the switch-actuating means to actuate switch means on the panel disposed substantially at a right angle. Spring means maintain the switch-actuating means in a normally inoperative position. A pin connected to the thumb and finger-engaging member moves in an arcuate slot in the panel to restrict the reciprocating movement thereof. A ring and little finger-engaging member extends through an arcuate slot in the panel and is connected to other switch-actuating means pivotally mounted adjacent other switch means. Spring means maintain the other switch-actuating means in a normally inoperative position. Indicating means are actuated when the switch means are actuated at the same time which operates the identification system. An object of the present invention is to provide a positioning and actuating mechanism for properly positioning a person's palm in the palm-positioning area of an electronics module of an identification system.

Another object of the present invention is the provision of a positioning and actuating mechanism that will accommodate to the size of a person's hand.

A further object of the present invention is to provide a positioning and actuating mechanism that will actuate switch means when the person's palm has been properly positioned.

An additional object of the present invention is the provision of a positioning and actuating mechanism that includes indicating means to indicate that the palm has been properly positioned.

These and other objects of the present invention will appear more fully from description and the accompanying drawings illustrating preferred embodiments of the invention. It is to be understood that changes may be made from the exact details that are shown and described without departing from the principles of the invention.

DETAILED DESCRIPTION OF THE INVENTION

Figure 1:
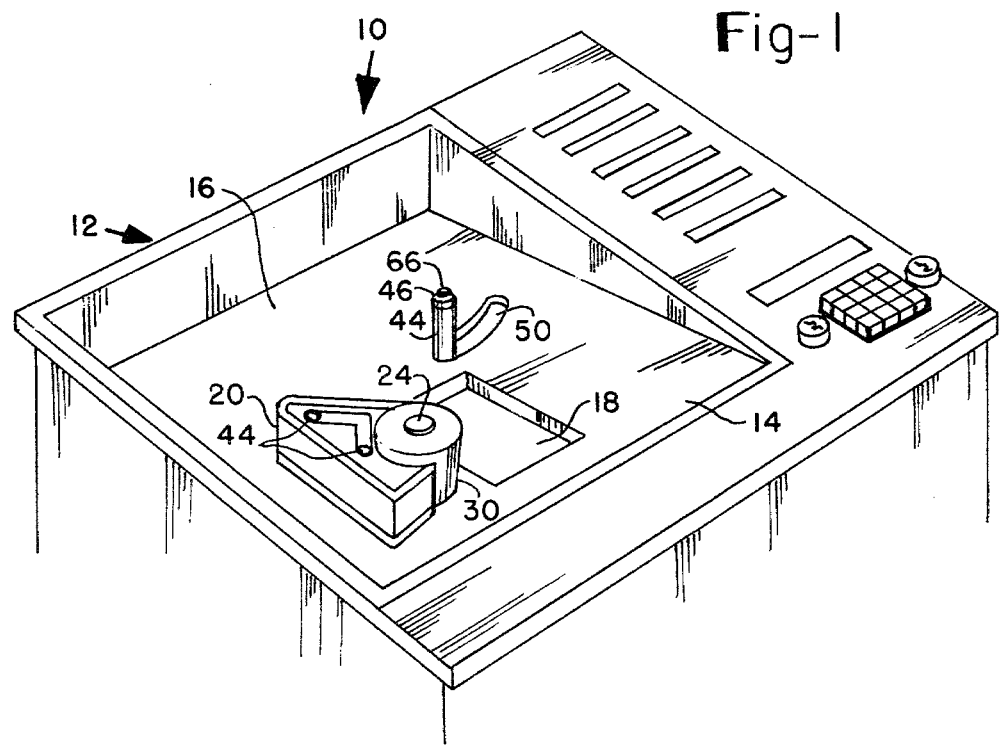
FIG. 1 is a part perspective view of the electronics module of the identification system.
Figure 2:
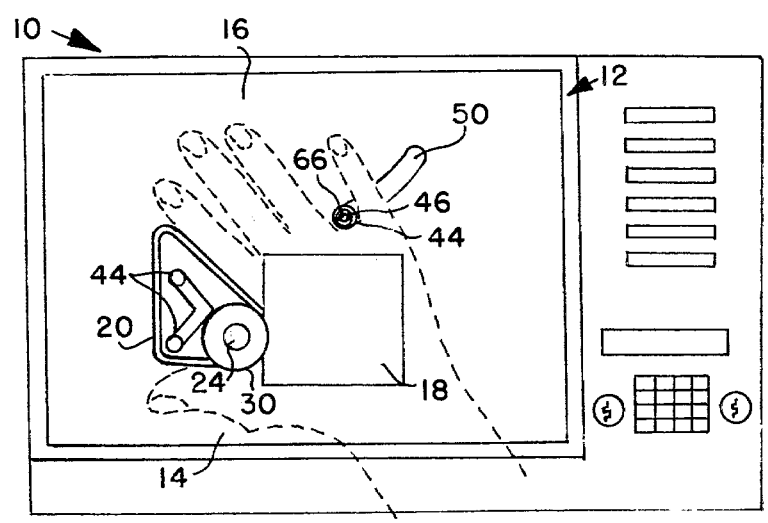
FIG. 2 is a part top plan view showing the palm-positioning area of the electronics module showing a person's hand in the palm-positioning area.
Figure 3:
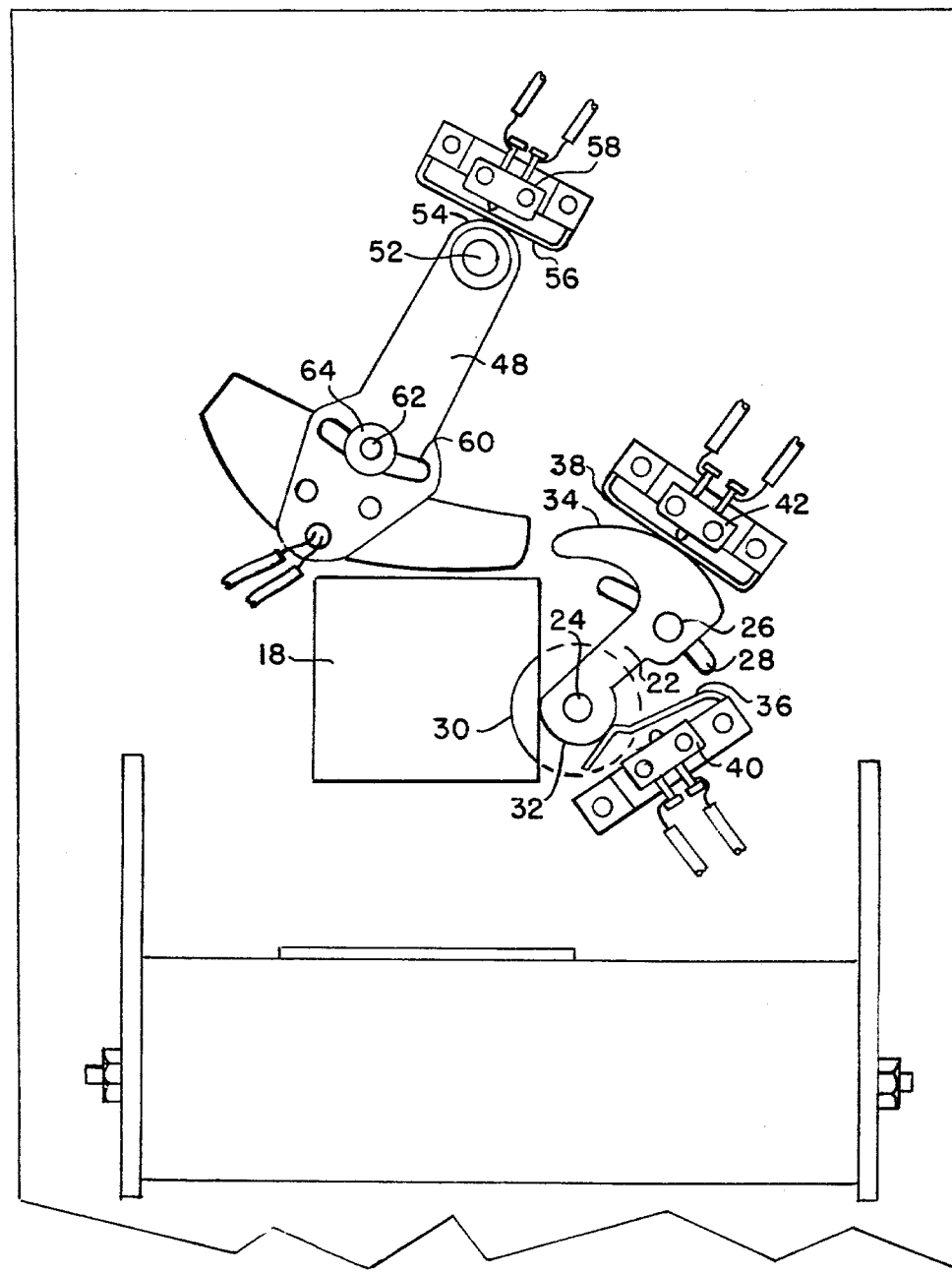
FIG. 3 is a bottom plan view showing the switch means and switch-actuating means.

A recognition data acquisition unit 10 houses the electronic circuitry and camera for taking a photograph of a palm of a person's hand, storing the information for identifying the palm and comparing the person's palm with the stored information identifying his palm to verify he is that person. It is important that the person's palm be properly and accurately positioned when his palm is photographed and to compare his palm with the stored information identifying his palm for purposes of verification.

A palm-positioning area 12 is located in the upper surface of unit 10 and it includes a metal plate 14 mounted in this upper surface. An inclined surface 16 has an opening 18 over which a person's palm is positioned. A thumb and forefinger-engaging member 20 is mounted to a switch-actuating member 22 by pivot 24. A pin 26 is secured to member 20 and extends through an arcuate slot 28 in plate 14. Pin 26 is also secured to switch-actuating member 22 and slot 28 enables the thumb and forefinger-engaging member 20 to turn about 30° to accommodate various hand sizes.

A roller 30 is mounted on pivot 24 and it and the sides of thumb and forefinger-engaging member 20 have a 15° angle to guide the palm into correct position over opening 18. Roller 30 facilitates positioning of thumb in engagement with member 20.

Radiussed surfaces 32 and 34 are provided on switch-actuating member 22 and they engage spring members 36 and 38 secured on plate 14 adjacent microswitches 40 and 42. Pivot 24 and pin 26 have some play so that spring members 36 and 38 keep switches 40 and 42 from being actuated until the thumb and forefinger-engaging member 20 is engaged by the thumb and forefinger of a person's hand whereupon the play in pivot 24 and pin 26 enables radiussed surfaces 32 and 34 to push against spring members 36 and 38 and actuate switches 40 and 42 to actuate indicating lamps 44 in thumb and forefinger-engaging member 20.

A roller 44 is mounted on a tubular pin 46 that is connected to switch-actuating member 48 and pin 46 extends through an arcuate slot 50 in plate 14. Switch-actuating member 48 is pivotally mounted via pivot pin 52 to plate 14 and it has a radiussed surface 54 engaging spring member 56 mounted on plate 14 adjacent microswitch 58. Spring member 56 keeps microswitch 58 from being actuated except when roller 44 is positioned between the ring finger and little finger therebetween. Arcuate slot 50 enables roller 44 to accommodate different hand sizes and switch-actuating member 48 has an arcuate slot 60 therein similar to that of slot 50 in plate 14 to enable switch-actuating member 48 to move to the position that roller 44 and pin 46 are moved to by a person's ring and little finger. A pin 62 is mounted on plate 14 and extends through slot 60 and a washer 64 is mounted on pin 62 to maintain switch-actuating member 48 on plate 14.

Sufficient play is provided by pin 52 and slot 60 to enable switch-actuating member 48 to be moved against spring member 56 when roller 44 is positioned at the inner ends of the ring and little fingers of a person's hand thereby actuating switch 58 which energizes indicating lamp 66 mounted at the outer end of tubular pin 46 signifying proper positioning of the right section of a person's palm over opening 18.

In operation, a person positions the thumb and forefinger along the inclined sides of thumb and forefinger-engaging member 20 and the inner ends of the ring and little fingers are positioned in engagement with roller 44 to properly position the person's palm over opening 18. The person then applies pressure to member 20 and roller 44 whereupon switch-actuating members 22 and 48 are moved so that radiussed surfaces 32, 34, and 54 move spring members into engagement with microswitches 40, 42, and 58 thereby actuating them which energizes lamps 44 and 66 indicating proper positioning of the person's palm over opening 18 and activating the identification system to store in coded form the palm of the person or to compare the person's stored coded palm for positive identification.

Thus, the present invention provides a unique palm-positioning and system-actuating mechanism for properly positioning a person's palm in the palm-positioning area of an electronics module of an identification system and for activating the means for storing in coded form the palm of the person or for comparing the person's palm with the stored coded palm for positive identification. Although the invention has been explained with reference to a particular embodiment, it is to be appreciated that various adaptations and modifications may be made without departing from the appended claims.

The invention is claimed in accordance with the following:

1. A palm-positioning and system-actuating mechanism for properly positioning a person's palm and for actuating a system for coding the palm or comparing the coded palm for purposes of identification, said mechanism comprising:
   a plate having a palm-positioning area, said plate having an opening and an arcuate slot adjacent said opening in said palm-positioning area;
   a thumb and forefinger-engaging member, pivot means pivotally mounting said thumb and forefinger-engaging member onto said plate adjacent said opening; first switch-actuating means mounted onto said pivot means and having radiussed surface means thereon;
   second switch-actuating means mounted onto said plate by pivot pin means and having a ring and little finger-engaging member thereon extending through said arcuate slot and radiussed surface means thereon;
   switch means mounted on said plate means adjacent said radiussed surface means;
   spring means mounted on said plate means between said switch means and said radiussed surface means;
   said radiussed surface means engaging said spring means so that said spring means normally prevent said switch-actuating means from actuating said switch means, said pivot means and pivot pin means having play therein to enable said switch-actuating means to actuate said switch means via said radiussed surface means moving said spring means against said switch means when a person's thumb and forefinger engage said thumb and forefinger-engaging member and the ring and little finger engage said ring and little finger-engaging member and move said switch-actuating means thereby properly positioning the person's palm over said opening.

2. A palm-positioning and system-actuating mechanism according to claim 1 wherein said thumb and forefinger-engaging member includes roller means mounted on said pivot means.

3. A palm-positioning and system-actuating mechanism according to claim 2 wherein said thumb and forefinger-engaging member and said roller means have slanted surfaces to guide the person's palm over said opening.

4. A palm-positioning and system-actuating mechanism according to claim 1 wherein said plate has another arcuate slot therein and a pin member extends through said other arcuate slot and is connected to said thumb and forefinger-engaging member and said first switch-actuating means.

5. A palm-positioning and system-actuating mechanism according to claim 1 wherein said ring and little finger-engaging member includes a roller member.

6. A palm-positioning and system-actuating mechanism according to claim 4 wherein said radiussed surface means on said first switch-actuating means are located adjacent said pivot means and said pin member and said spring means and switch means are located substantially at right angles relative to one another.

7. A palm-positioning and system-actuating mechanism according to claim 1 wherein said second switch-actuating means includes another arcuate slot therethrough and a pin member mounted on said plate extends through said other arcuate slot and includes washer means to secure said second switch-actuating means on said plate.

8. A palm-positioning and switch-actuating mechanism according to claim 1 wherein indicating lamps are connected to said switch means and said indicating lamps are energized upon actuating of said switch means to indicate proper positioning of the person's palm over said opening.

* * * * *